United States Patent
Kim et al.

(10) Patent No.: US 7,727,136 B2
(45) Date of Patent: Jun. 1, 2010

(54) APPARATUS AND METHOD FOR SEPARATING MATERIAL BY SIZE USING A ROTATING DRUM HAVING MULTIPLEX AXES OF ROTATION

(75) Inventors: Young-rok Kim, Yongin-si (KR); Kak Namkoong, Yongin-si (KR); Jun-hong Min, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 291 days.

(21) Appl. No.: 11/682,673

(22) Filed: Mar. 6, 2007

(65) Prior Publication Data

US 2007/0238598 A1    Oct. 11, 2007

(30) Foreign Application Priority Data

Apr. 6, 2006    (KR) ............... 10-2006-0031491

(51) Int. Cl.
*B04B 7/12*    (2006.01)
*B04B 13/00*    (2006.01)

(52) U.S. Cl. .................. 494/10; 494/19; 494/27; 494/37; 494/43

(58) Field of Classification Search .......... 494/19, 494/27–30, 31–34, 43, 47, 67–73, 80, 10, 494/37; 422/72
See application file for complete search history.

(56) References Cited

U.S. PATENT DOCUMENTS

| | | | | |
|---|---|---|---|---|
| 1,853,249 A | * | 4/1932 | Ainlay | 494/43 |
| 1,935,547 A | * | 11/1933 | Dryhurst | 494/67 |
| 2,022,926 A | * | 12/1935 | Schlank | 494/32 |
| 4,296,882 A | * | 10/1981 | Kobayashi | 494/18 |
| 4,361,480 A | * | 11/1982 | Corbus et al. | 494/80 |
| 4,874,358 A | * | 10/1989 | Brimhall et al. | 494/37 |
| 5,141,486 A | * | 8/1992 | Antwiler | 494/37 |
| 5,151,368 A | * | 9/1992 | Brimhall et al. | 435/286.7 |
| 5,368,541 A | * | 11/1994 | Knelson | 494/80 |
| 5,501,522 A | * | 3/1996 | Tung | 366/219 |
| 5,888,184 A | * | 3/1999 | Wardlaw | 494/10 |
| 6,593,143 B1 | * | 7/2003 | Gordon | 436/45 |
| 7,419,463 B2 | * | 9/2008 | Aagaard et al. | 494/34 |
| 2005/0051466 A1 | * | 3/2005 | Carter et al. | 494/10 |
| 2007/0238598 A1 | * | 10/2007 | Kim et al. | 494/43 |

* cited by examiner

*Primary Examiner*—Charles E Cooley
(74) *Attorney, Agent, or Firm*—Cantor Colburn LLP

(57) ABSTRACT

An apparatus and method for centrifugally separating particles by both weight and size include a rotating drum rotating about a second rotating axis disposed perpendicularly to a first rotating axis, and includes an inlet, at least one rotating plate and an outlet. The inlet injects a test material. The rotating plate extends radially outward toward an inner surface of the rotating drum from the second rotating axis and has one or more configurations of protruded and recessed portions formed on a surface thereof. The rotating plate receives the test material on a surface thereof. The outlet discharges separated test material.

11 Claims, 4 Drawing Sheets

APPARATUS AND METHOD FOR SEPARATING MATERIAL BY SIZE USING A ROTATING DRUM HAVING MULTIPLEX AXES OF ROTATION

This application claims priority to Korean Patent Application No. 10-2006-0031491, filed on Apr. 6, 2006, and all the benefits accruing therefrom under 35 U.S.C. §119, the contents of which in its entirety are herein incorporated by reference.

BACKGROUND OF THE INVENTION

1. Field of the Invention

The present invention relates to an apparatus and method for separating materials by weight and size using centrifugal force.

2. Description of the Related Art

Conventional methods of separating materials by size include filtering and size-separation chromatography. Centrifugal separation is the use of centrifugal force to separate components in a material by the specific gravity of the components. Centrifugal separators can be classified into centrifugal settlers and centrifugal filters. Centrifugal settlers have a sealed rotating drum within which a material is separated into residual layers. A centrifugal filter, on the other hand, has an open rotating drum with apertures through which liquid or small particles can pass through to the outside of the drum. The centrifugal filter contains a filtering plate with apertures formed therein, whereby a rotating force is applied perpendicularly to the filtering plate.

Accordingly, in the prior art, there is no centrifugal separation method or apparatus which use a plate without apertures to centrifugally separate materials.

Thus, there is a need for an apparatus method for separating material by size, quickly and easily using a plate without apertures to centrifugally separate materials.

BRIEF SUMMARY OF THE INVENTION

During the process of developing a centrifugal separator and method of not only separating materials through centrifugal force, but also separating particles by size, the inventors of the present invention discovered that a centrifugal separator equipped with a rotating plate having one or more different configurations having protruded and recessed portions is able to quickly and easily separate particles by size, thus arriving at the present invention.

The present invention provides an apparatus and method for quickly and easily separating particles by weight and size using centrifugal force.

According to an exemplary embodiment of the present invention, there is provided an apparatus for centrifugally separating particles by both weight and size, the apparatus including a rotating drum rotating about a second rotating axis disposed perpendicularly to a first rotating axis, the rotating drum and the second rotating axis rotating about the first rotating axis, the rotating drum including: an inlet for injecting a test material; at least one rotating plate extending radially outward toward an inner surface of the rotating drum from the second rotating axis, the rotating plate having one or more configurations selected from the group consisting of protruded and recessed portions formed on a surface thereof, the rotating plate receiving the test material on a surface thereof from the inlet; and an outlet for discharging separated test material.

The apparatus may further include a first driving member for imparting rotating force about the first rotating axis.

The apparatus may further include a second driving member for imparting rotating force about the second axis.

The first rotating axis and the second rotating axis may be connected by a joint, for example, a universal joint.

The rotating drum may include an inlet for injecting a test material, at least one rotating plate extending radially outward toward an inner surface of the rotating drum from the second rotating axis and having one or more configurations selected from the group consisting of protruded and recessed portions formed on a surface thereof, and an outlet for discharging separated test material.

In another exemplary embodiment of the present invention, the rotating drum may include a detector which detects a signal from the surface of the rotating plate. The detector detects a surface signal of the rotating plate, that is, a signal which arises from the material which is separated through the structure of the rotating plate. The signal may be, for example, an optical or electrical signal, but is not limited thereto. The detector may be an optical detector which optically detects an optical signal from the surface of the rotating plate. The optical detector may include a light source for emitting an excitation light on the rotating plate, and a light detector that measures the signals from the substrate.

The light detector may include a motor to move radially across the rotating plate from the second rotating axis. The detector may be a CD or DVD reader.

According to another exemplary embodiment of the present invention, there is provided a method of separating particles in a test material for use with an apparatus for centrifugally separating particles by both weight and size, the apparatus including a rotating drum rotating about a second rotating axis disposed perpendicularly to a first rotating axis, the rotating drum including: an inlet for injecting the test material; at least one rotating plate extending radially outward toward an inner surface of the rotating drum from the second rotating axis and having one or more configurations selected from the group consisting of protruded and recessed portions formed on a surface thereof, the rotating plate receiving and rotating the test material on a surface thereof; and an outlet for discharging separated test material, wherein the method includes: injecting the test material through the inlet to provide the test material on the rotating plate; orbiting the rotating drum about the first rotating axis and providing a first centrifugal force to the test material on the rotating plate in a direction along the second rotating axis; and rotating the rotating drum about the second rotating axis and providing a second centrifugal force to the test material on the rotating plate in a direction perpendicular to the second rotating axis.

The injecting of the test material may be performed through the inlet when the rotating drum is or is not detached from the apparatus.

The orbiting of the rotating drum about the first rotating axis and the providing of a first centrifugal force to the test material on the rotating plate in a direction along the second rotating axis may be performed sequentially or simultaneously. The rotating drum may be made to orbit about the first rotating axis through a first driving member, such as a motor. Particles in the test material separate and settle on the floor of the rotating plate through the first centrifugal force. Resultantly, the particles are divided in a first stage by means of the first centrifugal force.

The rotating of the rotating drum about the second rotating axis and the providing of a second centrifugal force to the test material on the rotating plate in a direction perpendicular to the second rotating axis may be performed sequentially or simultaneously. A second driving member such as a motor may rotate the rotating drum about the second rotating axis. Particles of the test material may be separated by being moved by the second centrifugal force outward from the center of the rotating plate. Also, the protruded and recessed portions of the rotating plate may have more than one structure, and cause the particles to be separated in a further stage by their size. Thus, the material is separated in a second stage by the second centrifugal force.

The orbiting of the rotating drum about the first rotating axis and the providing of a first centrifugal force to the test material on the rotating plate in a direction along the second rotating axis, and the rotating of the rotating drum about the second rotating axis and the providing of a second centrifugal force to the test material on the rotating plate in a direction perpendicular to the second rotating axis may be performed sequentially or simultaneously.

The method may further include injecting a washing liquid through the inlet to wash remaining test material from the rotating plate, when the first centrifugal force and the second centrifugal force are simultaneously provided.

The method may further include stopping the providing of the first centrifugal force and recovering the remaining test material from the rotating plate. In this case, the separated particles on the rotating plate are recovered while administering of the second centrifugal force is in progress or has been stopped.

The method may further include: labeling particles for separation with a detectable labeling material; and detecting the remaining test material on the rotating plate. The labeling material may be a fluorescent material. The detecting of the material remaining on the rotating plate may be performed using an optical detecting method. When the labeling material is a fluorescent material, the detecting of the material remaining on the rotating plate may be performed through fluorescent detecting.

BRIEF DESCRIPTION OF THE DRAWINGS

The above and other aspects, features and advantages of the present invention will become more apparent by describing in more detail exemplary embodiments thereof with reference to the attached drawings, in which.

DETAILED DESCRIPTION OF THE INVENTION

Figure 1:
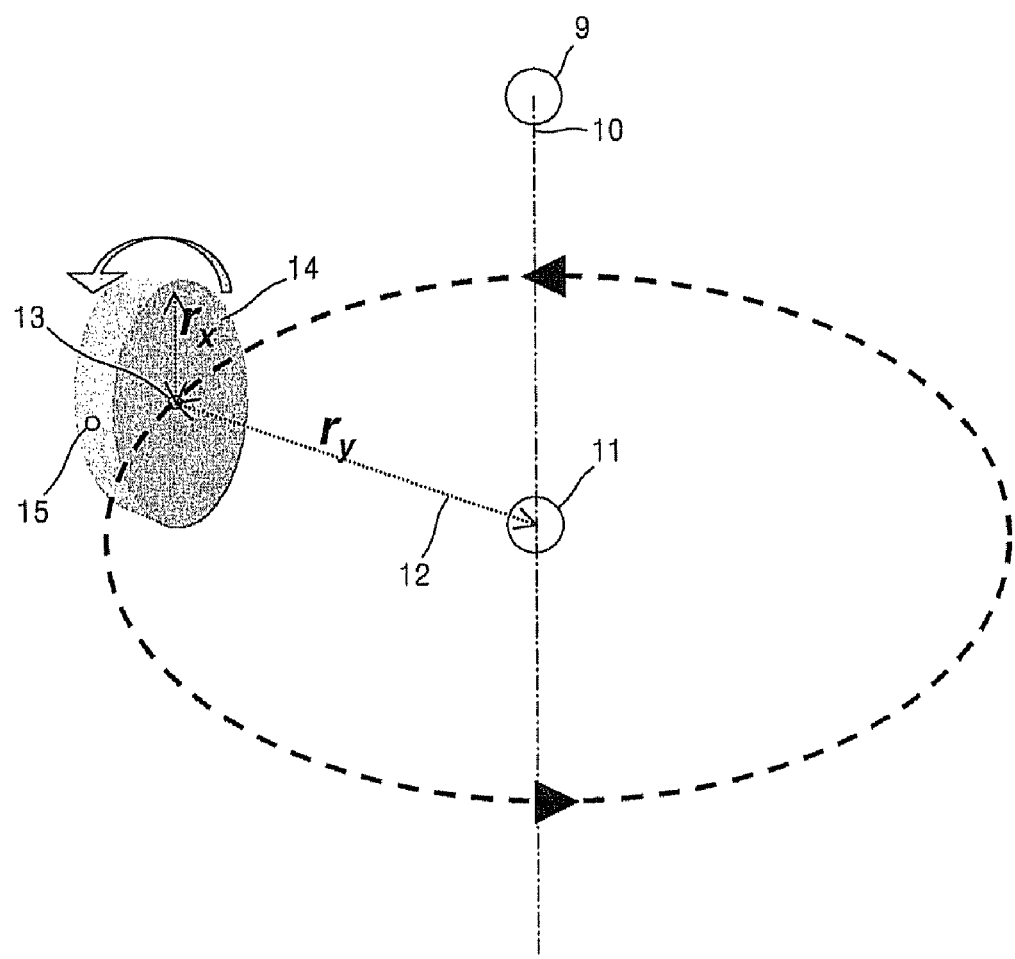
FIG. 1 is a schematic drawing of an apparatus for centrifugal separation according to an exemplary embodiment of the present invention.

The present invention will now be described more fully with reference to the accompanying drawings, in which exemplary embodiments of the invention are shown.

This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that when an element or layer is referred to as being "combined to" another element or layer, the element or layer can be directly combined to another element or layer or intervening elements or layers. In contrast, when an element is referred to as being "directly combined" to another element or layer, there are no intervening elements or layers present. Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or." The terms "comprising" and "including" are to be construed as open-ended terms (i.e., meaning "including, but not limited to").

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

FIG. 1 is a schematic diagram of an apparatus for centrifugal separation according to an exemplary embodiment of the present invention. Referring to FIG. 1, a rotating drum 14 rotates about the center of a second rotating axis 12 which is disposed perpendicularly to a first rotating axis 10. The rotating drum 14 includes an inlet (13) to inject test material, one or more rotating plates which hold the test material on their surfaces and extend radially toward the inner walls of the rotating drum 14 and extend from the second rotating axis, and an outlet (15) for discharging the separated test material. Still referring to FIG. 1, the rotating drum 14 rotates about the second rotating axis 12 in a counterclockwise direction and thus the rotating drum 14 rotates about the first rotating axis 10 in the counterclockwise direction. That is, the second rotating axis 12 also rotates counterclockwise and thus orbits the rotating drum 14 in the same direction. In FIG. 1, rx is the radius of the rotating drum 14, and ry is the distance from the surface of the rotating drum 14 to the first rotating axis 10. The first and second rotating axes 10 and 12 are connected to driving means (9 and 11) as known by those skilled in the pertinent art.

Figure 2:
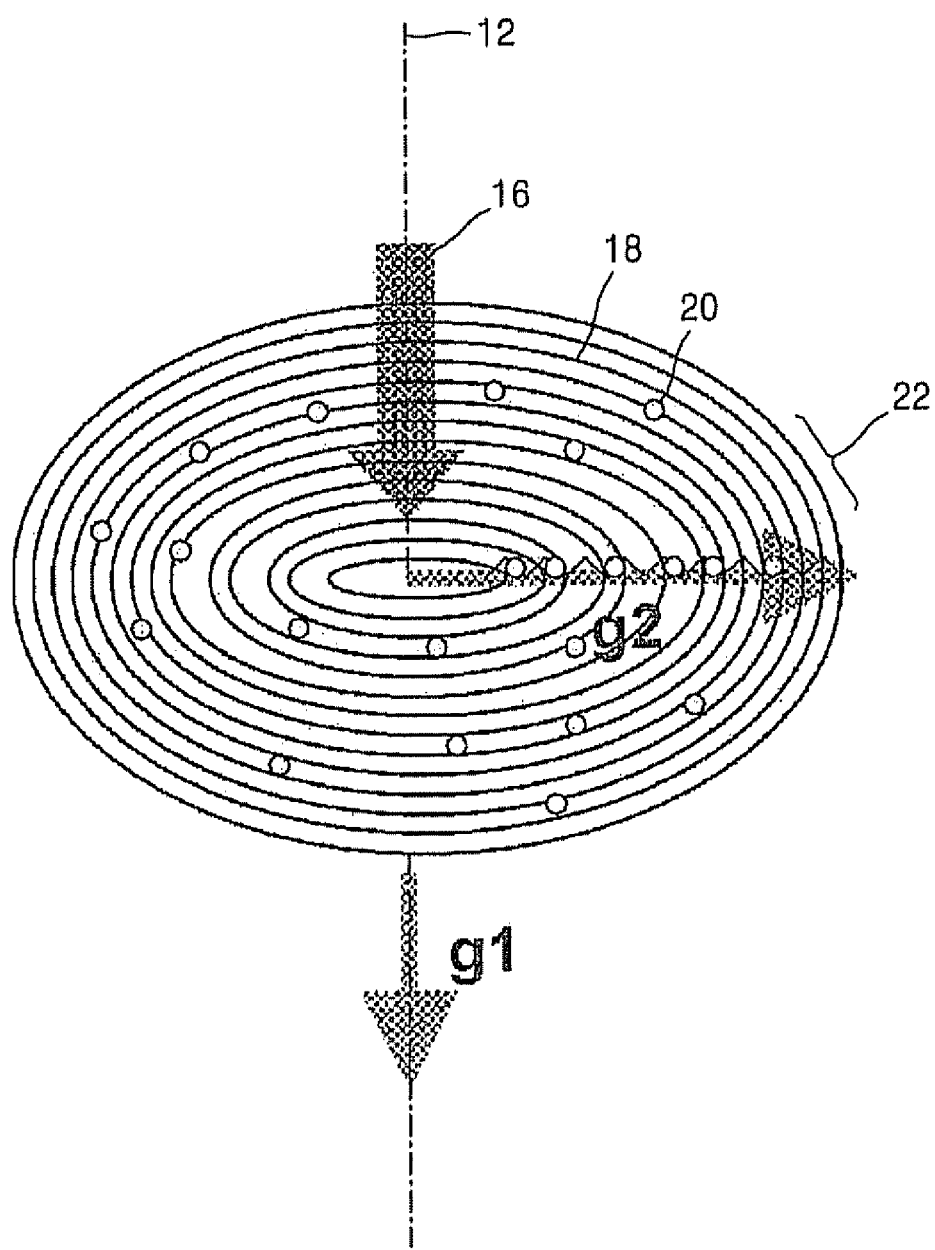
FIG. 2 is an exemplary diagram of a rotating plate in a rotating drum of the centrifugal apparatus in FIG. 1, according to an exemplary embodiment of the present invention.

FIG. 2 is an exemplary diagram of a rotating plate 22 in the rotating drum 14 of the centrifugal apparatus in FIG. 1, according to an exemplary embodiment of the present invention. The rotating plate 22 is disposed perpendicularly to the second rotating axis 12, from which it extends radially outward, and has concentric protruded and recessed portions 18 formed on the surface thereof. The test material is injected through the inlet (not shown) onto the surface of the rotating plate 22 in the direction of an arrow 16 and coinciding with the second rotating axis 12. A first centrifugal force g1 created by rotation about the first rotating axis 10 and a second centrifugal force g2 created by rotation about the second rotating axis 12 separate particles 20 of the test material between the protruded and recessed portions 18.

Figure 3A:
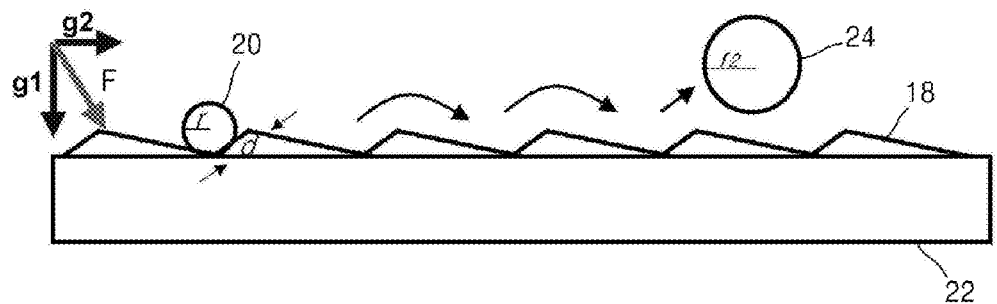
FIGS. 3A-3C are schematic drawings for explaining a method of separating test material, according to an exemplary embodiment of the present invention.
Figure 3B:
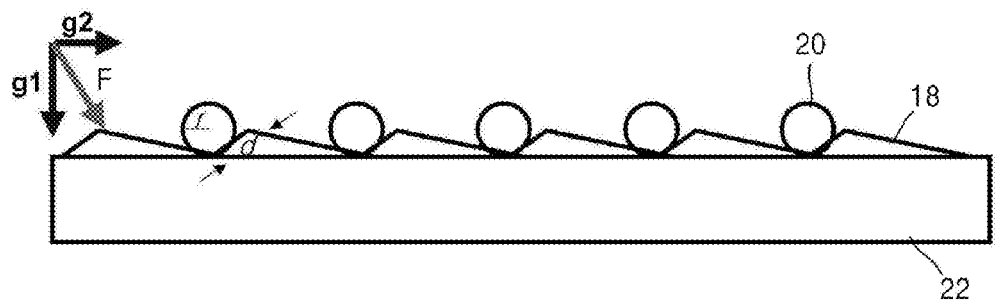
Figure 3C:
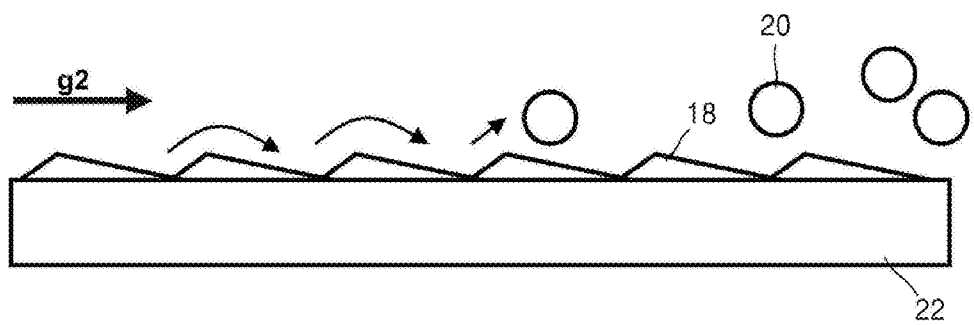

FIGS. 3A-3C are schematic drawings for explaining a method of separating test material according to an exemplary embodiment of the present invention. Referring to FIGS. 3A-3C, particles from the test material injected through the inlet of the rotating drum 14 are acted upon by the first and second centrifugal forces g 1 and g 2 when the drum 14 is orbited and rotated about the first and second rotating axes 10 and 12, respectively. The first and second centrifugal forces g 1 and g 2 combine to create a resultant force F. The protruded portions 18 are formed at a uniform height (d) extending from a major surface defining the rotating plate 22, so that particles 24 with a radius r 2 (which are larger than particles 20 with a radius r) oppose less resistance against the second centrifugal force g 2 such that they move radially outward on the plate 22 (as shown in FIG. 3A). The result is that only particles of a certain size remain on the plate 22 (as shown in FIG. 3B). Next, if the first centrifugal force g 1 is removed, the application of only the second centrifugal force g 2 causes the remaining particles 20 on the plate 22 to move outward and the remaining particles 20 can be collected (as shown in FIG. 3C).

Referring to FIGS. 1-2 and 3A-3C, the rotating plate 22 extends radially toward the inner wall of the rotating drum 14, and receives the test material on the surface when the test material is injected through the inlet. When the rotating drum 14 orbits about the first rotating axis 10, the rotating plate 22 orbits with the rotating drum 14. Here, the test material on the rotating plate 22 receives the first centrifugal force g 1 along the direction of the second rotating axis 12. The rotating plate 22 may be formed of an arbitrary material, whether transparent or opaque. The inlet and the outlet may be formed in arbitrary locations in the rotating drum 14. The inlet may be formed around the second rotating axis 12—that is, at the rotating central portion of the rotating plate 22, and the outlet may be formed in a distal position with respect to the central rotating portion of the rotating plate 22 such as at the inner sidewall of the rotating drum 14.

The rotating plate 22 may be disposed at a predetermined angle, preferably, a perpendicular angle, extending from the second rotating axis 12.

The rotating plate 22 may have one or more configurations selected from the group consisting of protruded and recessed portions formed on a surface thereof. The configuration may have both of the protruded and recessed portions, but may have only one of the portions in alternative exemplary embodiments. The rotating plate 22 may have protruded portions on its surface. Also, the rotating plate 22 may have recessed portions on its surface. The structure of the protruded and recessed portions may be arbitrarily formed. When the structure is a protruded portion, the structure may rise at an acute angle from the surface of the rotating plate 22, as illustrated in FIGS. 3A-3C. When the structure is a recessed portion, the structure may recess with an acute angle below the surface of the rotating plate. However, because the particles of material on the rotating plate 22 have two centrifugal forces g 1 and g 2 applied thereto by rotations about the first and second rotating axes 10 and 12, and are thus separated, the structure does not necessarily have to employ acute inclined angles. Also, the protruded and recessed portions may rise or recess from the surface of the rotating plate 22 at the same or different absolute heights. In the case of a structure with the same elevation or depression on a single rotating plate, it is easier for particles of the same size to concentrate on a single rotating plate 22.

The structure may employ concentric portions arranged from the second rotating axis 12.

The rotating plate 22 may have a motor (not shown) which allows it to rotate independently of the rotating drum 14 about the second rotating axis 12. Also, the outer edge of the rotating plate 22 farthest from the second rotating axis 12 may be in contact or sealed with the inner surface of the rotating drum 14. If the outer edge is in contact and sealed with the inner surface, part of the particles is separated on only one rotating plate 22. If the outer edge is not in contact with the inner surface, a portion of the particles may move onto adjacent rotating plates 22 also.

In an exemplary embodiment of the present invention, the rotating drum 14 is detachably connected to the apparatus. In this case, the injecting of test material through the inlet and the discharging of the same through the outlet may be made easier.

The exemplary method may further include injecting a washing liquid through the inlet to wash remaining test material from the rotating plate 22, when the first centrifugal force g 1 and the second centrifugal force and g 2 simultaneously provided.

The exemplary method may further include stopping the providing of the first centrifugal force g 1 and recovering the remaining test material from the rotating plate 22. In this case, the separated particles 20 on the rotating plate 22 are recovered while administering of the second centrifugal force g 2 is in progress or has been stopped.

The exemplary method may further include: labeling particles 20 for separation with a detectable labeling material; and detecting the remaining test material on the rotating plate 22. The labeling material may be a fluorescent material. The detecting of the material remaining on the rotating plate 22 may be performed using an optical detecting method. When the labeling material is a fluorescent material, the detecting of the material remaining on the rotating plate 22 may be performed through fluorescent detecting.

The test material may be arbitrarily chosen. For example, blood, containing cells of different sizes, or biological fluids may be used. Because different sized cells (e.g., including white blood cells, red blood cells, and platelets) are mixed in blood, the apparatus and method for centrifugal separation may be used to separate the types of cells. Also, the apparatus and method may be used to efficiently separate rare cells such as cancer cells, malignant microorganisms inherent in urine and other bodily fluids, and fractionate nucleic acids, proteins, polysaccharides, and other biological molecules and organelles.

Figure 4:
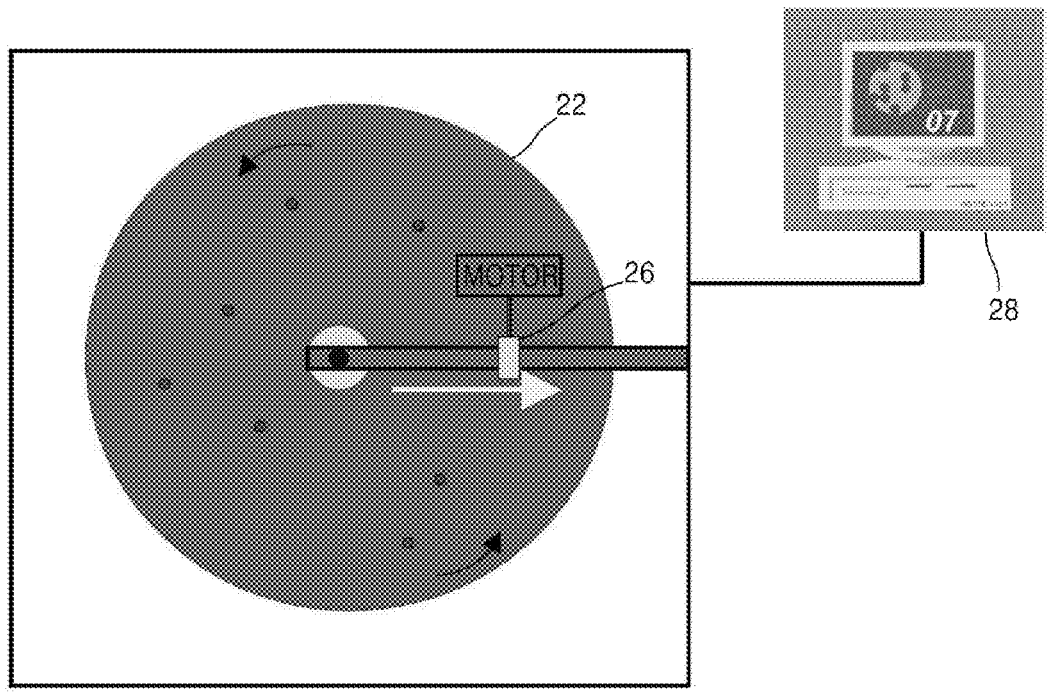
FIG. 4 is a detailed diagram of a rotating plate of an apparatus for centrifugal separation having a detector for detecting signals from the surface of the rotating plate, according to an exemplary embodiment of the present invention.

FIG. 4 is a detailed diagram of a rotating plate 22 of an apparatus for centrifugal separation having a detector for detecting signals from the surface of the rotating plate 22 according to an exemplary embodiment of the present invention. Referring to FIG. 4, a detector 26 capable of moving across the radius of the rotating plate 22 is provided. The detector 26 is connected to a computer 28.

The apparatus for centrifugal separation according to the present invention uses centrifugal force to separate test material particles not only by weight, but also by size. Because specific particles can be deposited on the rotating plate 22, an optical or other type of detector 26 can be used to easily detect the remaining particles. Accordingly, the apparatus for centrifugal separation according to the present invention can simultaneously perform separating and detecting for speedier and more accurate processing, thereby having increased efficiency.

In another exemplary embodiment of the present invention, the rotating drum 14 may include a detector 26 which detects a signal from the surface of the rotating plate 26. The detector 26 detects a surface signal of the rotating plate 22, that is, a signal which arises from the material which is separated through the structure of the rotating plate 22. The signal may be, for example, an optical or electrical signal, but is not limited thereto. In an exemplary embodiment, the detector 26 may be an optical detector which may include a light source for emitting an excitation light on the rotating plate 22, and a light detector which measures the signals from the substrate. The light detector may include a motor to move radially across the rotating plate 22 from the second rotating axis. The detector may be a CD or DVD reader.

The method according to the present invention uses centrifugal force to separate particles not only by weight but also by size, for more efficient separation.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus for centrifugally separating particles by both weight and size, the apparatus comprising:
    a rotating drum which rotates about a second rotating axis disposed substantially perpendicularly to a first rotating axis, wherein the rotating drum and the second rotating axis rotate about the first rotating axis, the rotating drum including:
        an inlet which injects a test material;
        at least one rotating plate extending substantially radially outward toward an inner surface of the rotating drum from the second rotating axis, the rotating plate having a plurality of at least one of a protruded portion and a recessed portion disposed on a surface thereof, the rotating plate receiving the test material on a surface thereof from the inlet, and wherein the plurality of at least one of a protruded portion and a recessed portion have substantially the same heights from a surface of the rotating plate;
        an outlet for discharging separated test material; and
        a detector which detects a signal from the surface of the rotating plate, wherein the detector includes a motor which enables the detector to move radially across the rotating plate.

2. The apparatus of claim 1, further comprising a first driving member for imparting a rotating force about the first rotating axis.

3. The apparatus of claim 1, further comprising a second driving member for imparting a rotating force about the second axis.

4. The apparatus of claim 1, wherein the rotating plate extends perpendicularly from the second rotating axis.

5. The apparatus of claim 1, wherein the plurality of at least one of a protruded portion and a recessed portion are arranged concentrically about the second rotating axis.

6. The apparatus of claim 1, wherein the detector is an optical detector.

7. A method of separating particles in a test material for use in an apparatus for centrifugally separating the particles by both weight and size,
    the apparatus including a rotating drum which rotates about a second rotating axis disposed substantially perpendicularly to a first rotating axis, wherein the rotating drum and the second rotating axis rotate about the first rotating axis, the rotating drum having an inlet which injects the test material; at least one rotating plate which extends substantially radially outward toward an inner surface of the rotating drum from the second rotating axis and having a plurality of at least one of a protruded portion and a recessed portion disposed on a surface thereof, the rotating plate receiving and rotating the test material on a surface thereof, and wherein the plurality of at least one of a protruded portion and a recessed portion have substantially a same height from the surface of the rotating plate; and an outlet for discharging separated test material,
    the method comprising:
    injecting the test material through the inlet to provide the test material on the rotating plate;
    orbiting the rotating drum about the first rotating axis and providing a first centrifugal force to the test material on the rotating plate in a direction along the second rotating axis;
    rotating the rotating drum about the second rotating axis and providing a second centrifugal force to the test material on the rotating plate in a direction substantially perpendicular to the second rotating axis;
    labeling particles of the test material with a detectable labeling material; and
    detecting labeled test material which remains on the rotating plate.

8. The method of claim 7, wherein the orbiting of the rotating drum and the rotating of the rotating drum are performed sequentially or simultaneously.

9. The method of claim 7, further comprising injecting a washing liquid through the inlet to wash remaining test material from the rotating plate, when the first centrifugal force and the second centrifugal force are simultaneously provided.

10. The method of claim 9, further comprising stopping the providing of the first centrifugal force and then recovering the remaining test material from the rotating plate.

11. The method of claim 7, wherein the labeling material is a fluorescent material, and the detecting of the remaining test material on the rotating plate is by fluorescent detecting.

* * * * *